United States Patent
Tokhtuev et al.

(10) Patent No.: US 7,142,299 B2
(45) Date of Patent: Nov. 28, 2006

(54) TURBIDITY SENSOR

(75) Inventors: Eugene Tokhtuev, Duluth, MN (US); Anatoly Skirda, Duluth, MN (US); Christopher J. Owen, Duluth, MN (US); William Christensen, Hibbing, MN (US)

(73) Assignee: Apprise Technologies, Inc., Duluth, MN (US)

( * ) Notice: Subject to any disclaimer, the term of this patent is extended or adjusted under 35 U.S.C. 154(b) by 190 days.

(21) Appl. No.: 10/990,532

(22) Filed: Nov. 18, 2004

(65) Prior Publication Data

US 2006/0103842 A1    May 18, 2006

(51) Int. Cl.
G01N 21/00    (2006.01)

(52) U.S. Cl. ...................................... 356/338
(58) Field of Classification Search ................ None
See application file for complete search history.

(56) References Cited

U.S. PATENT DOCUMENTS

| | | | |
|---|---|---|---|
| 3,888,269 A * | 6/1975 | Bashark | 134/57 D |
| 4,841,157 A * | 6/1989 | Downing, Jr. | 250/574 |
| 5,350,922 A | 9/1994 | Bartz | |
| 5,453,832 A | 9/1995 | Joyce | |
| 6,324,900 B1 | 12/2001 | Bruno et al. | |
| 6,842,243 B1 * | 1/2005 | Tokhtuev et al. | 356/338 |
| 2003/0117623 A1 * | 6/2003 | Tokhtuev et al. | 356/338 |
| 2003/0214653 A1 * | 11/2003 | Palumbo et al. | 356/338 |

FOREIGN PATENT DOCUMENTS

GB    1281342    10/1968

OTHER PUBLICATIONS

O'Dell, James A., "Appendix B. Determination of Turbidity By Nephelometry" EPA Guidance Manual Turbidy Provisions, Apr. 1999, pp. B1-B10.
"Water quality—Determination of turbidity", International Standard ISO 7027, Third Edition, Dec. 15, 1999, pp. 1-11.
"Omega Engineering—Turbidity Measurement", Omega.com , Nov. 5, 2004, pp. 1-5.
European Search Report dated May 4, 2006.

\* cited by examiner

Primary Examiner—Michael P. Stafira

(57) ABSTRACT

A turbidity measuring system is provided with a chamber and a sensor having a watertight housing, a light source, a first light focusing device for focusing a light emitted from the light source and passing therethough into a sample liquid, a second light focusing device for collecting at least one scattered light resulted form the focused light when passing the sample liquid, a photodiode for receiving the collected light thereby generating electronic signals, and an electronic board for processing the electronic signals. In particular, the watertight housing has a tilted bottom, the light detector includes at least two photodiodes for detecting separated turbidity measuring ranges, or an insert is placed at the bottom of the chamber having first and second insert channels each of whose axis pointing toward an axis of one of the cylindrically-shaped channels in the watertight housing in order to trap light.

28 Claims, 14 Drawing Sheets

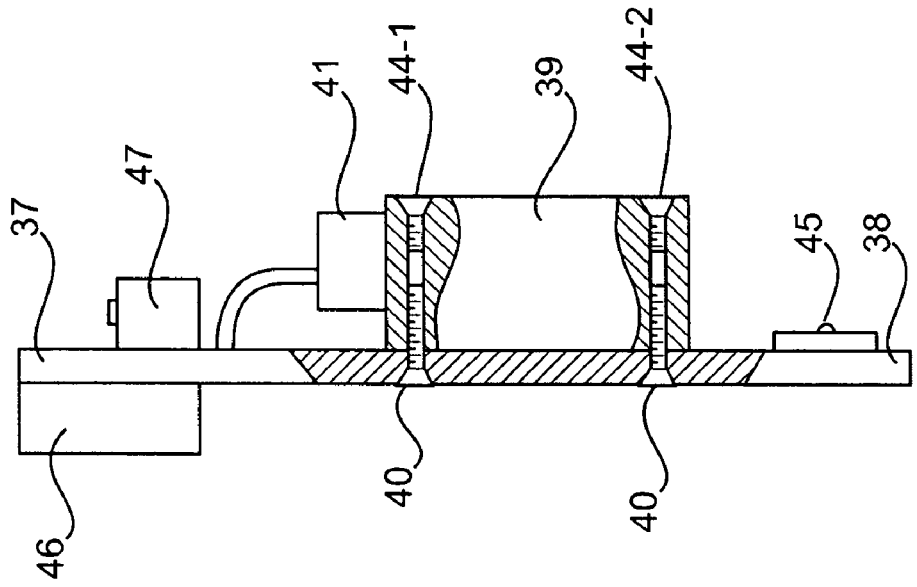
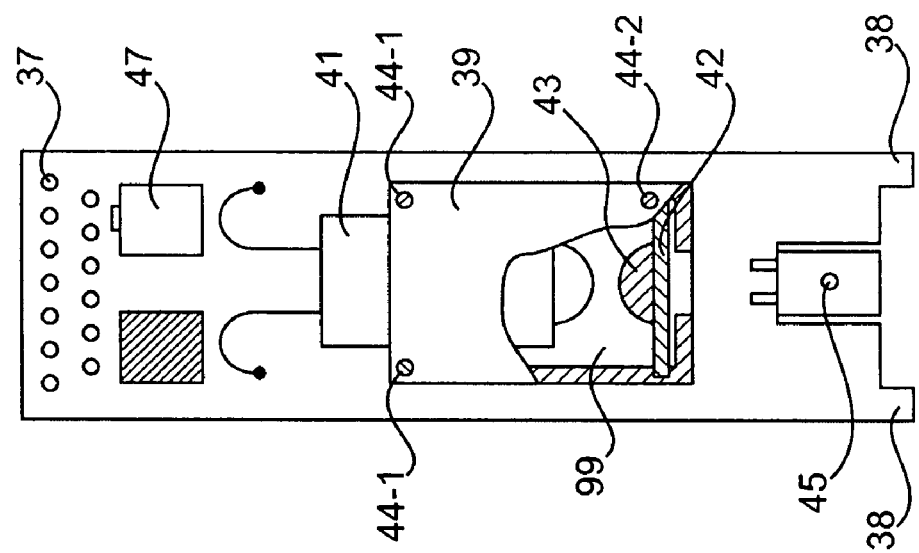
FIG. 3B
FIG. 3A

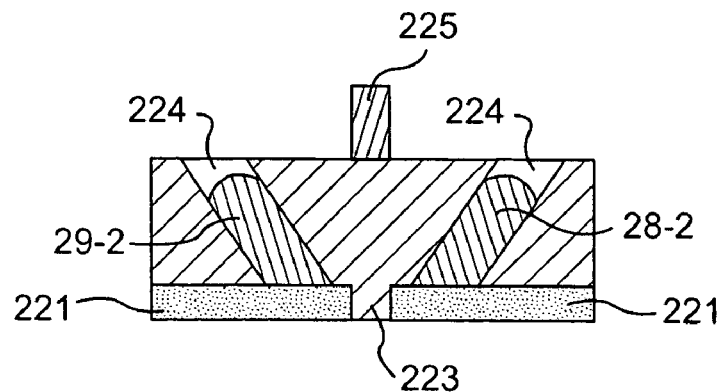
FIG. 12-A
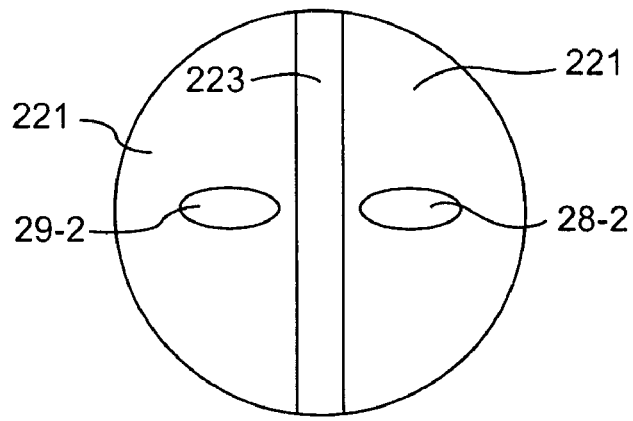
FIG. 12-B
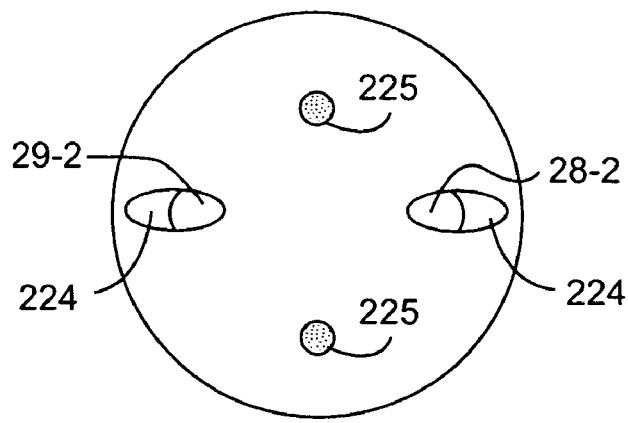
FIG. 12-C

TURBIDITY SENSOR

BACKGROUND OF THE INVENTION

1. Field of the Invention

The invention relates generally to a system for measuring turbidity of liquids, and more particularly to a system including a chamber for receiving a sample liquid, a cover for covering the chamber; and a sensor unit with its bottom immersed in the sample liquid.

2. Description of Related Arts

Turbidity sensors measure suspended matters in water that interfere with the passage of light through the water or in which visual depth is restricted. The turbidity may be caused by a wide variety of suspended materials, such as clay, silt, finely divided organic and inorganic matter, soluble colored organic compounds, plankton and other microscopic organisms and similar substances. Turbidity in water has public health implications due to the possibilities of pathogenic bacteria encased in the particles and thus escaping disinfection processes. Excessive amounts of turbidity also make water aesthetically objectionable. Turbidity of water is very important for evaluating the efficiency of the water treatment and water cleaning processes. The measurement unit for is nephelometric turbidity unit (NTU). An instrument called a nephelometer measures turbidity by measuring the amount of light scattered at an angle. The instrument is calibrated using samples of a standard solution such as formazin, a synthetic polymer. With a standardized procedure for preparing the stock solution of formazin with turbidity 4000 NTU, all other standards with different NTUs can be prepared by proportionally diluting the stock solution. Drinking water should not have turbidity above 1 NTU, although values up to 5 NTU are usually considered safe. Outside the U.S., this unit is usually called the FNU (formazin nephelometric unit).

The invention focuses on the in-line measurement turbidity of the water before and after processing in the water cleaning or water treatment facilities. There are two standard specifications for turbidity measurement that are generally in use worldwide. These are the International Standard ISO 7027 (Water quality—Determination of Turbidity, International Standard, Third Edition, 1999-12-15) and the USEPA 180.1 (Nephelometric Method 2130 B, Standard Methods for the Examination of Water and Wastewater, 1989). Both methods measure the intensity of light scattered at 90° to the path of incident light. The specification of the ISO standard is more stringent and requires the use of a monochromatic light source. This is a need for a greater reproducibility of measured values and for a greater agreement between existing measuring instruments, such as those provide by OMEGA Engineering, Inc. (Stamford, Conn., USA).

U.S. Pat. No. 6,324,900 describes a turbidity sensor with the capability of cleaning the interface surfaces immersed in water. This sensor operates by measuring the light that is scattered under a 90 degrees angle. The sensor has focusing converging lenses placed at a distance from the interface pieces. Such an optical design produces a divergent beam at the analytical area. It also describes another embodiment with the interface pieces made of optical fibers. Both embodiments are fail to provide the convergence of the optical beam as specified in the international standard ISO 7027.

The turbidity sensors described in U.S. Pat. No. 5,350,922 and U.S. Pat. No. 4,841,157 use LED light sources to operate with a broad range of scattering angles rather than at 90°, and their optical designs are significantly different from the requirements of the standard ISO 7027.

U.S. Pat. App. Pub. No. 2003/0214653 describes a turbidimeter having an arrangement of internal surfaces, optical surfaces, and optical restrictions to the field of view of both the illumination and the detector means to improve the lower detection limit of the turbidimeter by reducing the detected signal due to stray light. However, it has a pair of parallel channels, rather than two angled channels with a respective tiled axis with a window in parallel with the bottom of the sensor. Also, its light traps do not serve as a fluid inlet. In addition, it has only one photodiode to cover one testing range. Moreover, it does not comply with EPA 180.1 as it does not use any tungsten lamp as a light source. It also does not comply with ISO 7027 as the angle between the excitation beam and the measured scattered light is not in the range 90±2.5° as specified in the ISO 7027.

SUMMARY OF THE INVENTION

It is an object of the present invention to improve sensitivity of an industrial optical sensor for measuring turbidity and to provide an optical design, which allows installing an incandescent lamp according to the EPA 180.1 or installing an infrared LED according to the ISO7027.

It is an object of the present invention to provide a turbidity sensor that can be used with use two replaceable light sources to meet both EPA 180.1 and ISO 7027 methods.

It is another object of the present invention to improve the measurement range of a turbidity sensor so to provide several optical channels with different sensitivities.

It is another object of the present invention to improve a sample chamber for the turbidity sensor to eliminate stray light and decrease particle and bubble accumulation during operation. It is further object of the present invention to improve a turbidity measuring system with a faster time response or to decrease the flow rate with an identical response time as the prior art.

Other objects and advantages of the present invention may be seen from the following detailed description.

BRIEF DESCRIPTION OF THE DRAWINGS

FIG. 3A shows a side view of a first embodiment of a light source unit of the turbidity sensor shown in FIG. 1A; FIG. 3B shows another side view of the first embodiment of the light source unit shown in FIG. 3A.

FIG. 12A shows across-sectional view of a holder of the front end of the sensor according to the invention; FIG. 12B shows the bottom view of the holder; FIG. 12C shows the top view of the holder.

DETAILED DESCRIPTION OF THE INVENTION

Figure 1A:
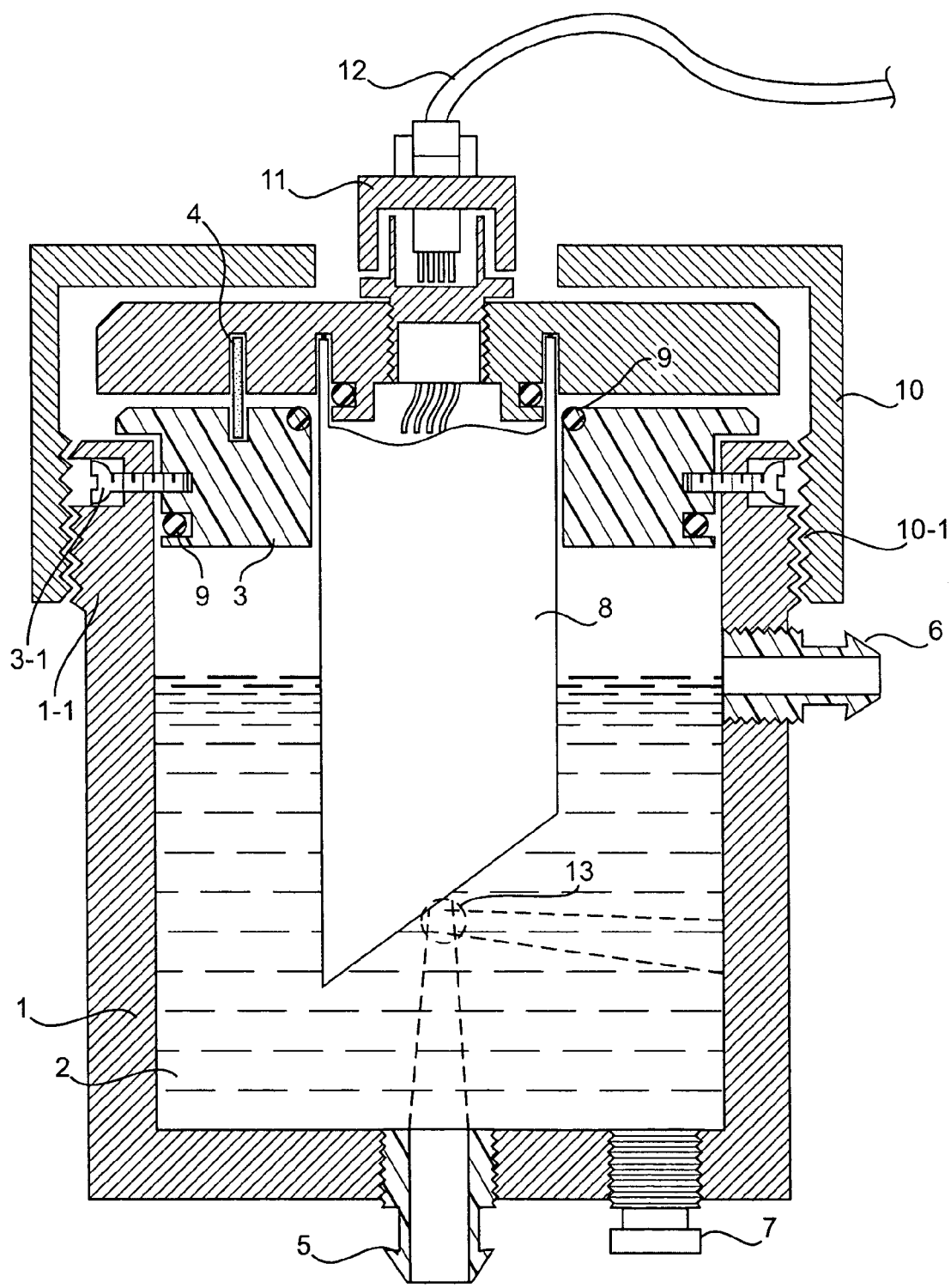
FIG. 1A shows a cross sectional view of a first embodiment of a turbidity sensor according to the invention.
Figure 1B:
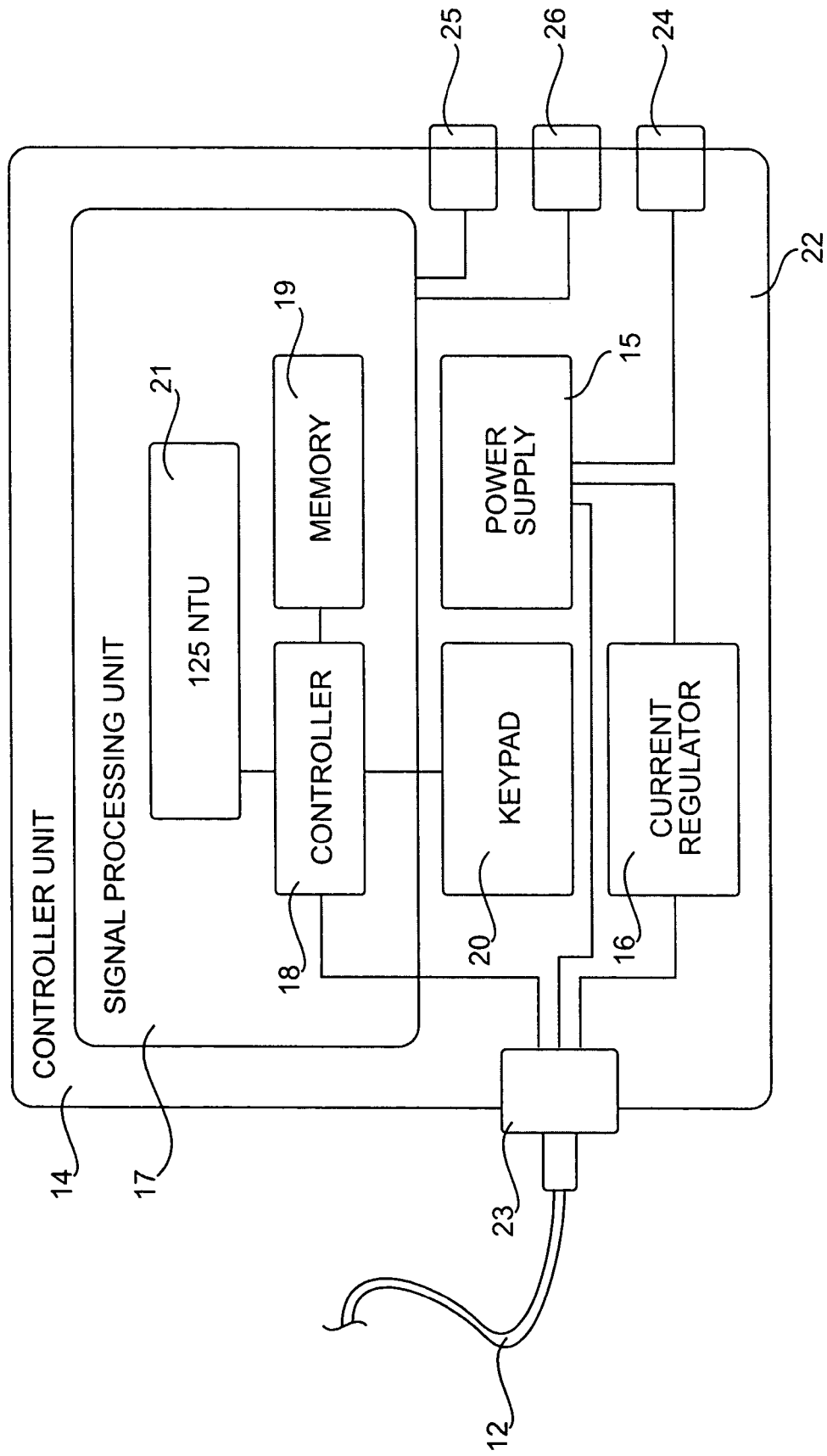
FIG. 1B shows the block diagram of a controller unit of the turbidity sensor shown in FIG. 1A.

In FIG. 1A, a turbidity sensor for testing a fluid sample 2 according to the present invention includes a sample chamber 1, a sensor unit 8, and a controller unit 14. The sample chamber 1 has at the top portion a mounting ring 3 for inserting the sensor unit 8 and a positioning pin 4, at least one inlet 5, at least one outlet 6, a plug 7 for releasing the sample 2 when necessary (e.g., cleaning), a chamber cap 10 with threads 10-1 on the inner surface to be screwed with threads 1-1 on the outer surface of the chamber 1, a cable connector 11 connecting a cable 12 to the sensor unit 8. The mounting ring 3 can be secured to the chamber 1 via a pair of screws 3-1. Some O-rings 9 are provided between the chamber 1, the mounting ring 3 and the sensor unit 8 to secure and seal them against each other. The cable 12 transfers signals between the sensor unit 8 and a controller unit 14 shown in FIG. 1B. The sample chamber 1 and the chamber cap 10 are made of an opaque material, such as aluminum or black PVC, to ensure that the photodiode receives only the light from the detector optical means 29. The sample chamber 1 has a diameter of 72 mm and a height of 140 mm. The mounting ring 3, the inlet 5, the outlet 6 are made of black PVC, nylon or other plastic. The O-rings 9 are made of elastic material, such as rubber.

The controller unit 14 includes a power supply 15, a current regulator 16, a signal processing unit 17 placed inside a controller housing 22. The controller housing 22 has a keypad 20, a display 21, and input connector 23 connecting the cable 12 to the controller unit 14. The signal processing unit 17 includes a memory 19 and a controller 18 which converting the analog signals produced by the photodiodes into digital signals in NTU based upon an equation or a converting table stored in the memory 19. The signal processing unit 17 can outputs the signals externally via a analog output connector 25 and a digital output connector 26. The power supply 15 may be battery or connected via a power connector 24 to an external power source. The power supply 15 outputs a power of 5 VDC to the detector unit 30 and via the current regulator 16 which adjusts the output current to be 228 mA to the light source unit 31.

Figure 2A:
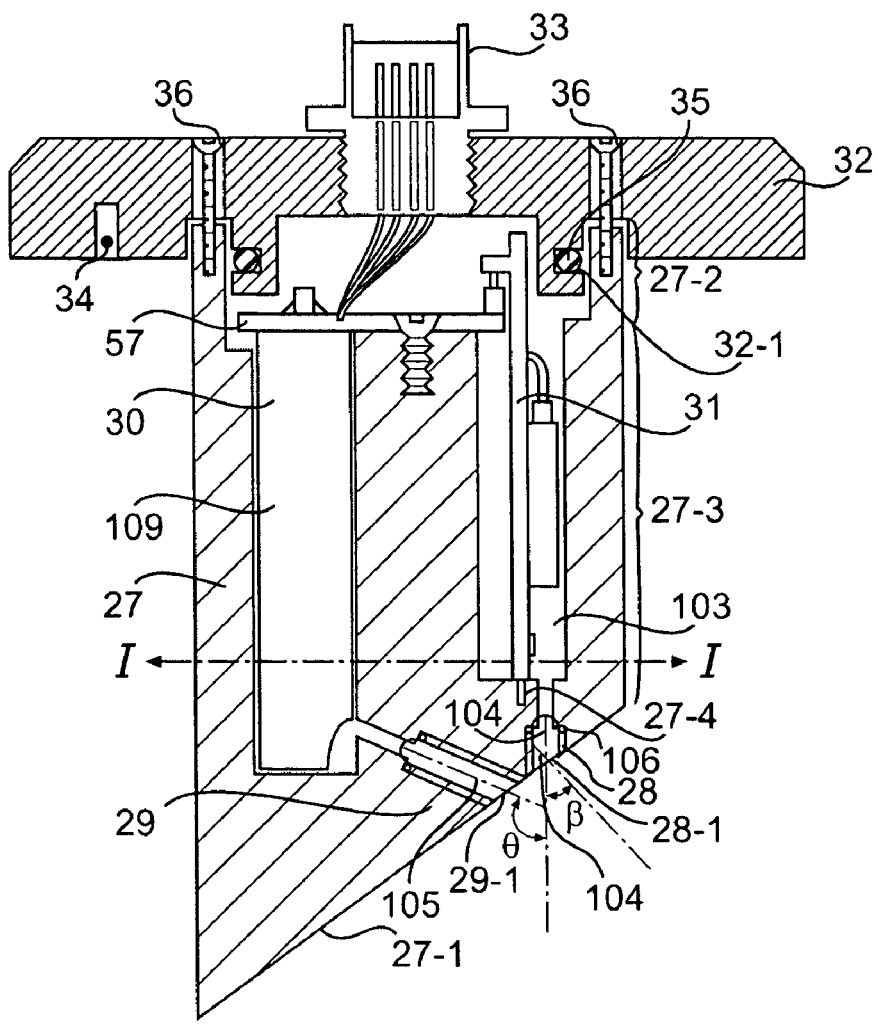
FIG. 2A shows a cross sectional view of a sensor unit of the turbidity sensor shown in FIG. 1A.
Figure 2B:
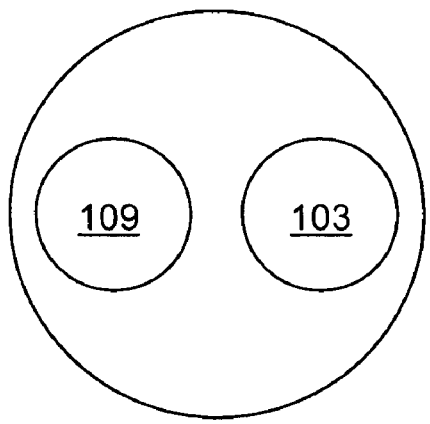
FIG. 2B shows a cross sectional view of the sensor unit shown in FIG. 2A taken along the line I—I.

The embodiment of the sensor unit 8 shown in FIG. 2 includes a cylindrical immersion body 27 to be immersed in the fluid sample 2, a sensor cover 32, a detector unit 30, and a light source unit 31. The cylindrical immersion body 27 (FIG. 8) has a tilted bottom part 27-1, a hollow top section 27-2 with a cavity 102 and a solid lower section 27-3 with two hollow cylindrical cavities 103, 109 for accommodating the detector unit 30 and the light source unit 31 therein respectively. The sensor cover 32 is secured to the immersion body 27 by a pair of screws 36. The cylindrical immersion body 27 is made of an opaque material with a diameter of 42 mm and a height of 108 mm. The tilted bottom part 27-1 is tilted with respect to a sample liquid surface/level about 30–60 degrees, and preferably 39 degrees such that any bubbles created there around can flow up to the a sample liquid surface, rather than stuck thereon. In another embodiment, the cylindrical immersion body 27 has a horizontal bottom part as the turbidity sensor described in U.S. patent application Ser. No. 10/315,142, which is hereby incorporated by reference. The invention applies the same measuring principle described in FIG. 1 of the U.S. patent application Ser. No. 10/315,142, i.e., measuring the light transits through the liquid sample, reaching the analytical area 13, and then scattered therein by 90°±2.5°

The cylindrical immersion body 27 is made of an opaque material, such as aluminum or black PVC, to ensure that the photodiode receives only the light from the detector optical means 29.

Figure 8:
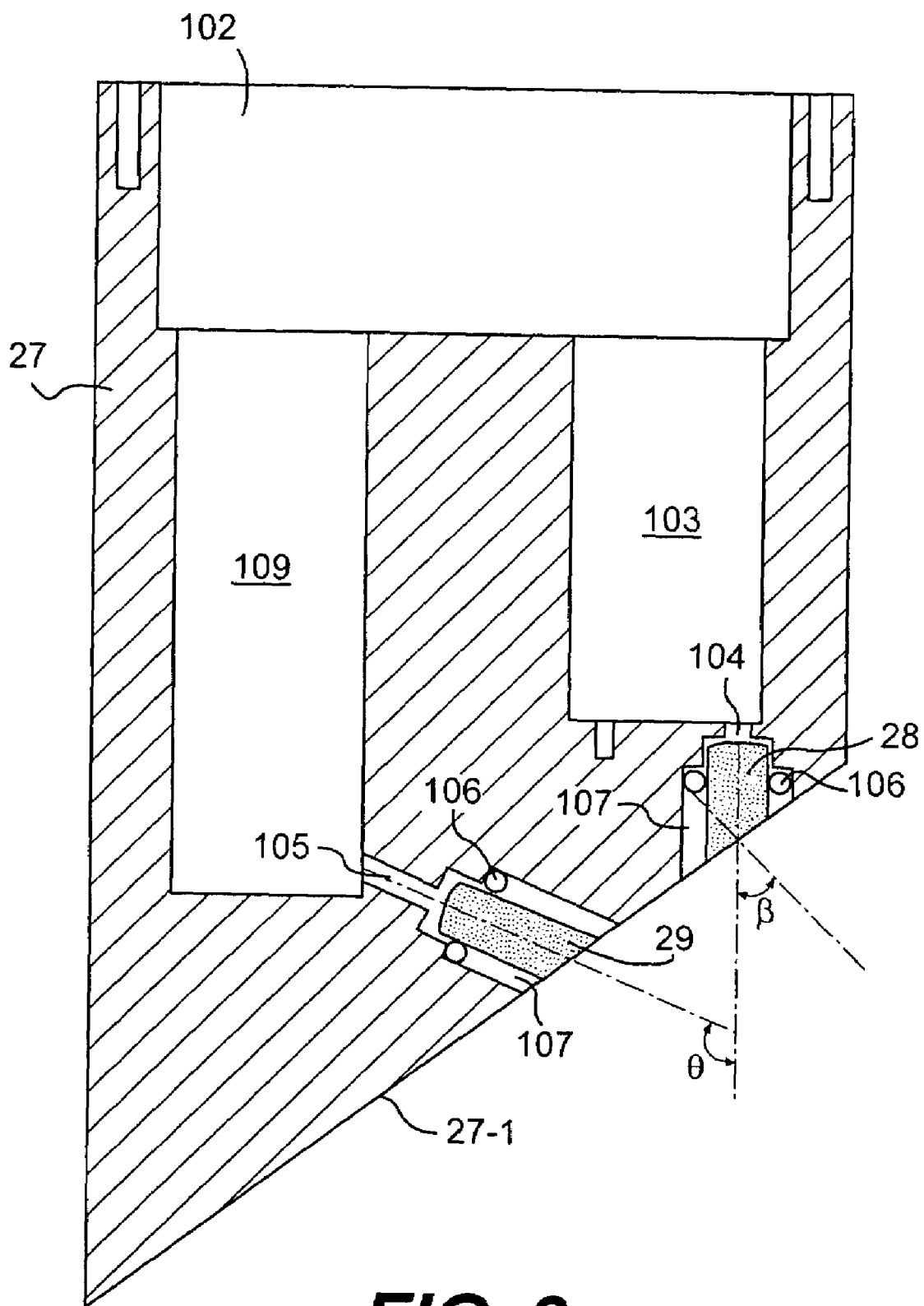
FIG. 8 shows a cross sectional view of the sensor unit of the turbidity sensor shown in FIG. 2A with only cavities and channels.

In FIG. 8, the cylindrical cavity 103 is optically communicating with a hollow cylindrical channel 104 for accommodating therein a light source optical means 28 (for focusing a light beam generated by the light source unit 31), and the cylindrical cavity 109 is optically communicating with a hollow cylindrical channel 105 for accommodating therein a detector optical means 29 (for collecting the scattered light by suspended matters in water). Both channels 104, 105 are tilted relatively to the tilted bottom part 27-1 at the same angle δ. The angle between the normal to the tilted bottom part 27-1 and the cylinder axis equals α(=90°−δ). The incidence angle α should be chosen in such way that the refraction angle β between the normal to the tilted bottom part 27-1 and the direction of beam in water should be 45°. The incidence angle α depends on the refractive index of the material used for light source optical means 28 and the detector optical means 29. The refraction angle β equals 45° if the incidence angle α corresponds to equation (1).

$$\mathrm{Sin}(\alpha) = \frac{N_p \cdot \mathrm{Sin}(45°)}{N_w} \quad (1)$$

Where $N_p$—refractive index of the material used for the prismatic focusing device $N_W$—refractive index of water The sensor cover 32 has at a top side a sensor connector 33 and at a lower side a hole or a notch 34 for receiving the positioning pin 4, and a cylindrical groove 32-1 with an O-ring 35 for receiving the hollow top section 27-2 of the immersion body 27. The cavity 103 has positioning holes 27-4 on the bottom and near the channel 105 for receiving a pair of positioning pin 38 of the light source unit 31.

The light source optical means 28 has a liquid-tight window 28-1 embedded in the tilted bottom part 27-1 to facilitate optical communication between the light source unit 31 and the liquid sample 2 outside of the immersion body 27, and the detector optical means 29 also has a liquid-tight window 29-1 embedded in the tilted bottom part 27-1 to facilitate optical communication between the detector unit 30 and the liquid sample 2 outside of the immersion body 27. The light source optical means 28 and the detector optical means 29 include a pair of prismatic focusing devices 28-2, 29-2 shown in FIG. 3 of the U.S. patent application Ser. No. 10/315,142. The light source optical means 28 and the detector optical means 29 are sealed watertight by O-rings 106 and a potting compound 107. For example, Resinlab EP1056LC Black carried by Ellsworth Adhesives in Germantown, Wis. may be used as the potting compound 107. In another embodiment, a half ball lenses replace the prismatic focusing device 28-2 and a half ball lenses and a ball lens shown in FIG. 4 of the U.S. patent application Ser. No. 10/315,142 replace the prismatic focusing device 29-2. Accordingly, each of the cylindrical channels 104, 105 is modified with a half spherical cavity at the end where meets the tilted bottom part 27-1.

Figure 4B:
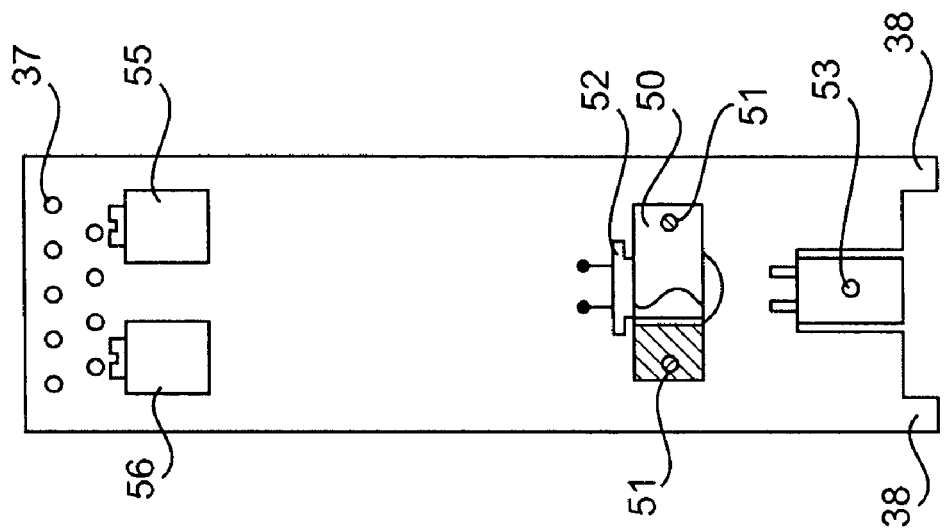
FIG. 4B shows another side view of the second embodiment of the light source unit shown in FIG. 4A.
Figure 4A:
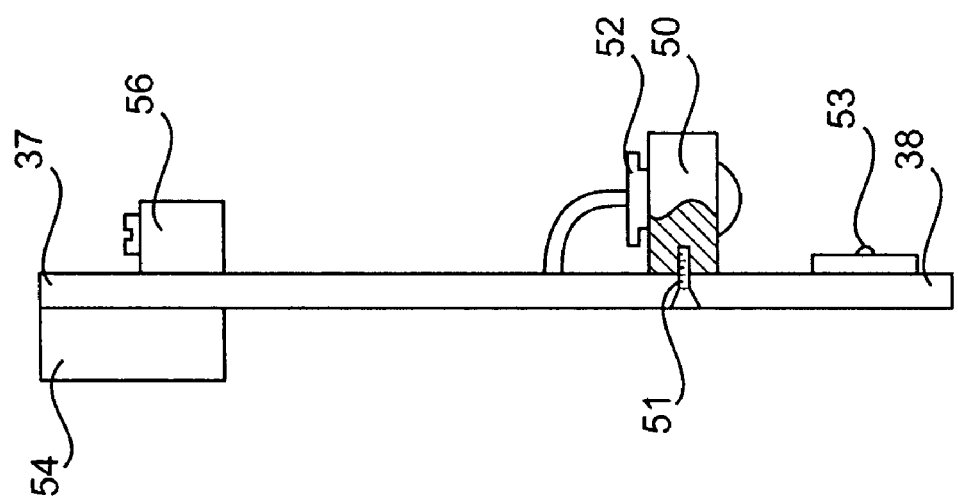
FIG. 4A shows a side view of a second embodiment of a light source unit of the turbidity sensor shown in FIG. 1A.

The light source unit 31 is designed to be easily replaced. FIGS. 3–4 show the front and side views of two embodiments of the light source unit 31. The replaceable light source 31 has a printed circuit board 37 with positioning pins 38 for positioning the printed board 37 inside the cavity 103 and with a light source holder 39 for holding a light source. The light source may be an incandescent lamp 41 or an LED 52 directed towards the channel 104. The incandescent lamp 42 is installed according to the EPA 180.1, and the infrared LED 52 is installed according to the ISO7027.

Turbidity sensing provides a quick, practical indication of the relative amount of suspended solids in the natural, pre and post processed water. The analytical devices for the turbidity measurements work usually apply two type of light sources: incandescent lamps or infrared light emitting diodes (LEDs). Incandescent lamps with a specified color temperature emit a broadband light with the maximum in visible range between 400 nm and 600 nm. Both types of light sources have different advantages for different industrial applications. The unified device, which can be easily modified from the incandescent lamp to the LED, will allow optimizing the measuring procedure according to the appropriate standards.

In FIG. 3B, four screws 40 fix the holder 39 to the printed circuit board 37, and a pair of set screws 44-1 fix the incandescent lamp 41 to the holder 39 for adjusting the position the incandescent lamp 41. The holder 39 has a channel 99 having an optical filter 42 and a focusing lens 43 glued on top of the optical filter 42, which is secured in the holder 39 with a pair of setscrews 44-2. The light source unit 31 has a reference detector 45 under the light source holder 39 and above the channel 104, a light source connector 46 for connecting the light source unit 31 to a disk-shaped detecting circuit board 57 of the detector unit 30, and a reference signal regulator 47. The reference detector 45 is directed approximately at 90 degrees to the optical axis of the excitation beam generated by the incandescent lamp 41. Incandescent lamps usually have a big variation in output intensity. To adjust the output intensity, the incandescent lamp 41 should be set in an appropriate position inside the holder 39 and secured with the setscrews 44. It is not recommended to adjust intensity using the lamp current because it might change a color temperature and impact the life time of the lamp. The position of the incandescent lamp 41 is adjusted such that the sensor output in the formazin turbidity solution 20 NTU equals to 2000 mV±200 mV for each light source board. The incandescent lamp 41 can be any electric lamp that produces light from an electrically heated filament and has a color temperature more than 2200° C. to comply with EPA 180.1 specifications. Preferably, the incandescent lamp 41 is Gilway L1025 by Gilway Technical Lamp (Woburn, Mass.), the reference detector 45 is photodiode PNZ335 by Panasonic, and the reference signal adjustment potentiometer 47 is SM4A101 by BC Components. The incandescent lamp 41 has a nominal current 240 mA but it operates with a regulated current 228 mA, which is lower than the nominal current. According to the technical data of the lamp manufacturer, such a mode of operation still produces a color temperature 2250° C. but extend the lamp lifetime to 30,000 hours. The light from the incandescent lamp 41 through the optical filter 42 and the focusing lens 43 reaches the light source optical means 28 to form an excitation beam. A small portion of light from the focusing lens 43, after multiple scattering and reflection inside the cavity 103, reaches the reference detector 45. The reference detector 45 then generates a reference electrical signal proportional to the intensity of the excitation beam. The reference signal adjustment potentiometer 47 changes a level of the reference electrical signal to set it equal to a nominal value. For EPA light source, this normal value is 1400 mV. For ISO light source, the nominal value of the reference electrical signal is 2000 mV. The controller 18 can recognize/determine, which light source is currently in operation based upon the nominal value. It allows automatically switching between EPA or ISO processing of the electrical signals which takes different linearization and calibration. In FIG. 4, a pair of screws 51 fix an LED holder 52 to the electrical printed board 37. The light source unit 31 has a reference detector 53, a light source connector 54 for connecting the light source unit 31 to a disk-shaped detecting circuit board 57 of the detector unit 30, a reference signal regulator 55, and a LED intensity adjustment potentiometer 56. The reference detector 53 is directed approximately at 90 degrees to the optical axis of the excitation beam generated by the LED 52. The LED 52 is a low-cost infrared light emitting diode with a narrow band spectral emission (e.g., PDI-E850 by Photonic Detectors, Inc.). The LED intensity adjustment potentiometer 56 may be SM4A101 by BC Components. The light from the LED 52 reaches the light source optical means 28 to form an excitation beam. The current through the LED 52 is adjusted such that the sensor output in the Formasin turbidity solution 20 NTU equals to 2000 mV±200 mV for each light source board. A small portion of the light from the LED 52, after multiple scattering and reflection inside the cavity 103, reaches the reference detector 47. The reference detector 47 generates a reference electrical signal proportional to the intensity of the excitation beam. For ISO light source, the nominal value of the reference electrical signal is 2000 mV.

Figure 5:
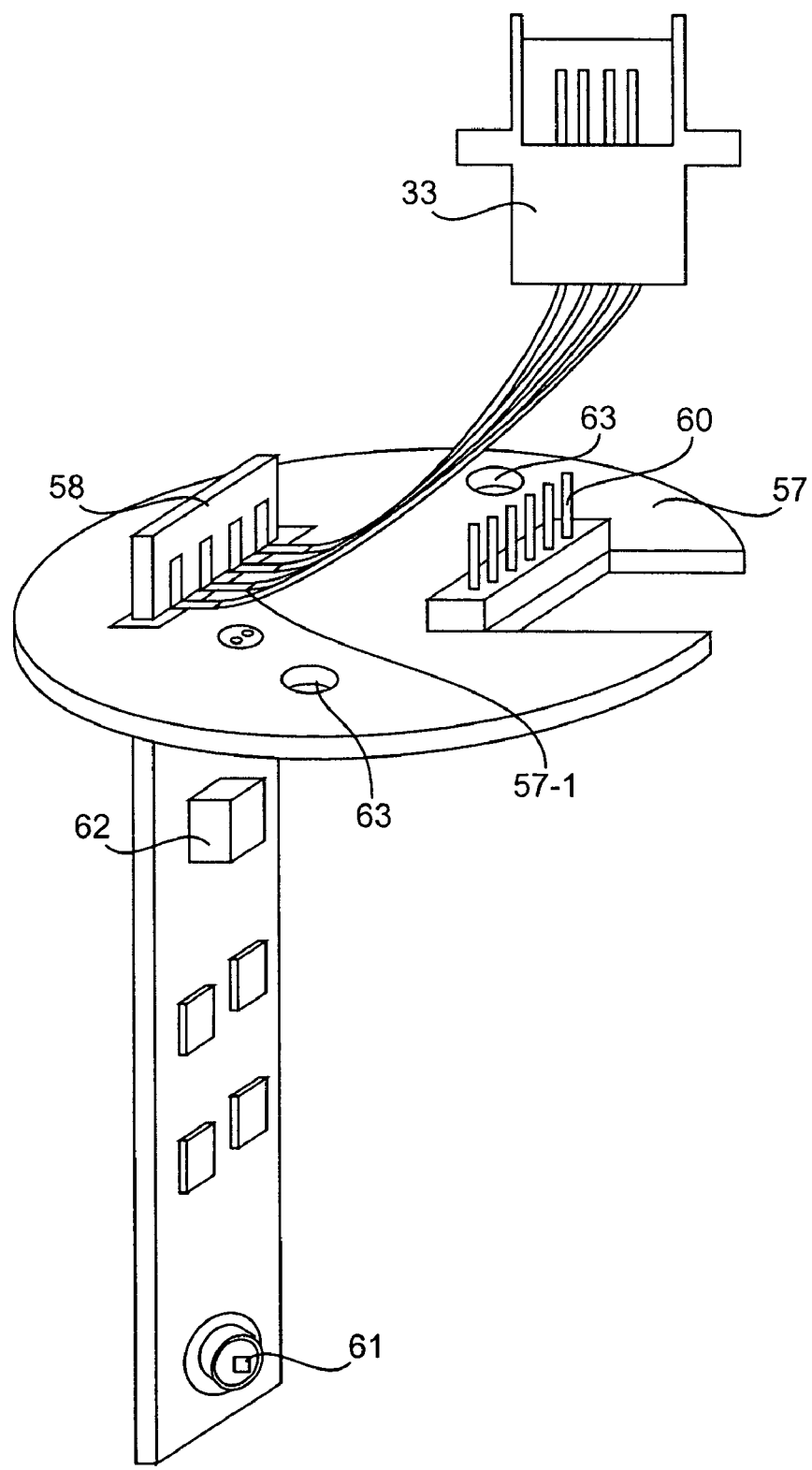
FIG. 5 shows a prospective view of a first embodiment of a detector unit of the turbidity sensor shown in FIG. 1A.

In FIG. 5, the detector unit 30 has a disk-shaped detecting circuit board 57 snuggly fitted in the hollow top section 27-2 of the immersion body 27. The detector unit 30 has a rectangular detecting circuit board 58 soldered onto the disk-shaped detecting circuit board 57 via a slot 57-1 in a perpendicular manner. A detector unit connector 60 is soldered on the disk-shaped detecting circuit board 57 to be interlocked with the light source connector 46 in FIG. 3 or 54 in FIG. 4. The disk-shaped detecting circuit board 57 has mounting holes 63 for screwing at least one screw 30-1 from top down into the solid lower section 27-3 of the immersion body 27 so as to mount the detector unit 30 into the immersion body 27. The detector unit 30 has a cylindrical brass shield 71 wrapping around the rectangular detecting circuit board 58 and soldered onto the disk-shaped detecting circuit board 57 to be snuggly fitted with the cavity 109. At least one photodiode 61 for measuring radiation entered via the detector optical means 29 is soldered on the lower portion of the detecting circuit board 58. The cylindrical brass shield 71 has a cut or opening on the lower portion in front of the photodiode to allow a scattered light to transmit from the detector optical means 29 on the photodiode 61. An output signal adjustment potentiometer 62 is set on the detecting circuit board 58 to compensate variations in photodiode sensitivity and to adjust an amplification coefficient of a preamplifier on the detecting circuit board 58. The output signal adjustment potentiometer 62 is SM4A103 by BC Components.

Figure 6:
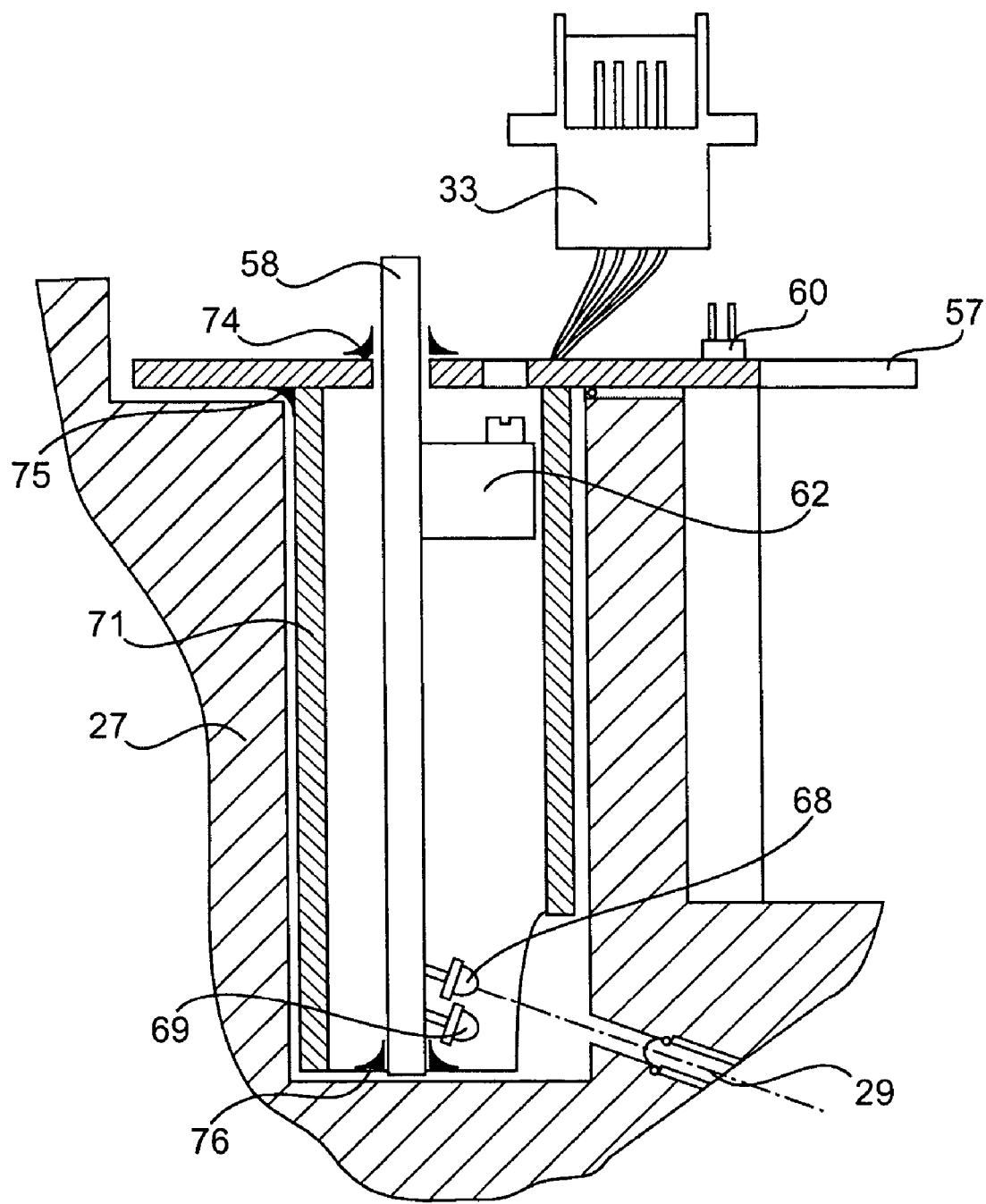
FIG. 6 shows a prospective view of a second embodiment of a detector unit of the turbidity sensor shown in FIG. 1A.
Figure 7A:
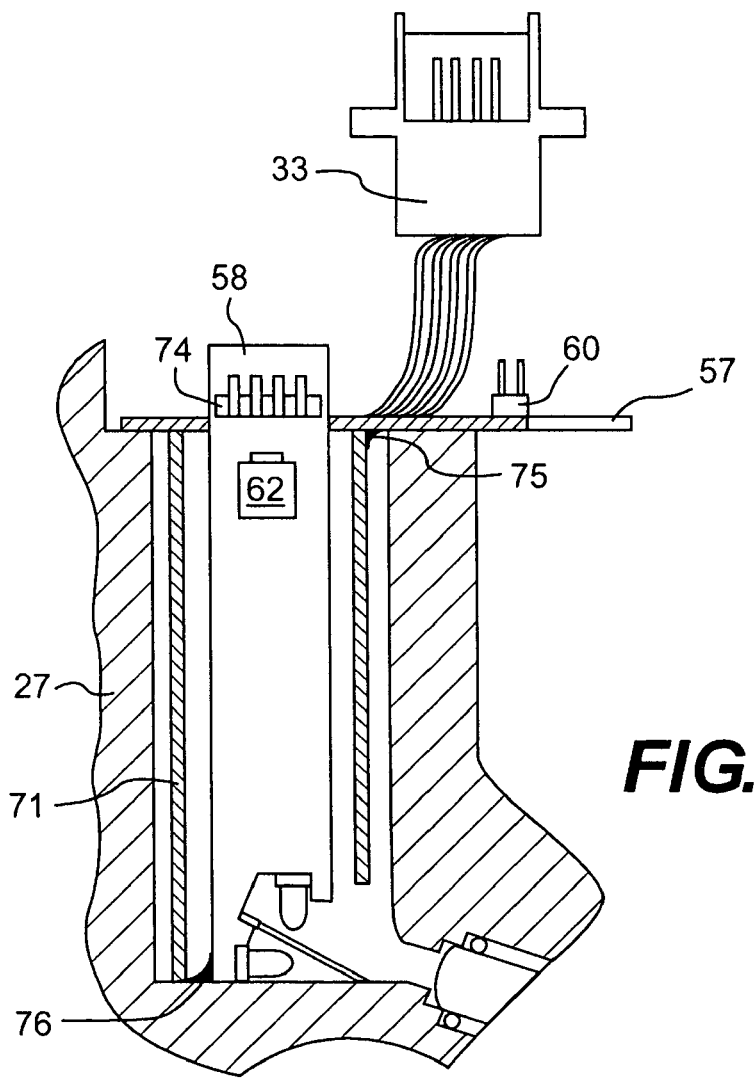
FIG. 7 shows a prospective view of a third embodiment of a detector unit of the turbidity sensor shown in FIG. 1A.
Figure 7B:
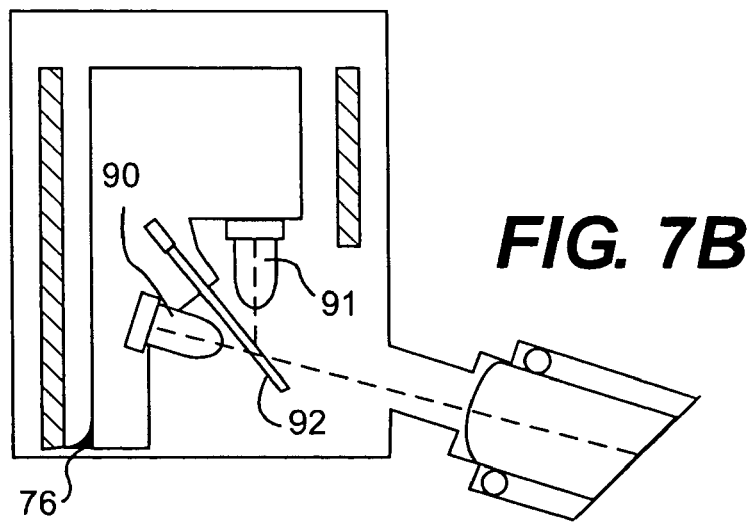

The embodiment shown in FIG. 6 includes two photodiodes 68, 69 for detecting light or different ranges. For example, the photodiode 68 is silicon photodiode with a broad spectral range (e.g., PN323BPA-ND by Digi-Key in Thief Rever Fall, Minn.), which detects 0–20 NTU. The photodiode 69 is a VTP3310LA, which detects 20–200 NTU. In other words, the photodiode 68 is aligned with the axis of the channel 105 to measure more than 80% of radiation, and the photodiode 69 has a smaller size and it is placed right below the photodiode 68 to measure less than 10% radiation. In another embodiment shown in FIG. 7, a plate-shaped beam splitter 92 made of a 0.5 mm thick polycarbonate plate is placed between the photodiodes 90, 91 with 39 degrees from their axes while the axes of the photodiodes 90, 91 cross each other at 78 degrees. The beam splitter-photodiode assembly is then placed after the detector optical means 29 such that a photodiode 91 collects more than 80% and a photodiode 90 collects less than 10% radiation The photodiode 91 is tilted down for 12 degrees with its axes directed along the axes of the detector optical means 29. The photodiode 90 is set vertically to collect radiation reflected from the beam splitter 92.

FIG. 6 also shows the place of soldering in the detector unit 30. The rectangular detecting circuit board 58 is soldered onto the disk-shaped detecting circuit board 57 via a first soldering 74. The cylindrical brass shield 71 is soldered onto the disk-shaped detecting circuit board 57 via a second soldering 75. The detecting circuit board 58 is soldered to the cylindrical brass shield 71.

FIG. 8 shows a cross sectional view of the sensor unit of the turbidity sensor shown in FIG. 2A with only cavities and channels.

Like the turbidity sensor described in U.S. patent application Ser. No. 10/315,142, the turbidity sensor of the invention has the light source optical means 28 and the detector optical means 29 placed in the two cylindrical channels 104, 105 respectively. Each of the cylindrical channels 104, 105 has a flat end which tilts relatively to its own cylinder axis with an angle so as to be in parallel with the tilted bottom part 27-1. Each of the light source optical means 28 and the detector optical means 29 include windows or focusing members sealed with O-rings. The cylindrical channels 104, 105 have portion with a smaller, nominal or larger diameter to support and the respective means therein and to seal the respective means in conjunction with the O-rings. If the channels 104, 105 have a larger diameter, they may be filled with epoxy from the O-rings to the surface of the tilted bottom part 27-1.

Each of the channels 104, 105 has a conical shape with a top of the cone directed to the point of intersection of the optical axes of the light source optical means 28 and the detector optical means 29. As shown in FIG. 1A, the channels 104, 105 point towards and define an analytical area 13, and the inlet 5 points toward the channel 104 to increase the testing efficiency. The inlet 5 also points toward the analytical area 13 defined by overlapping a first optical path of the light emitted from the light source and passing through the light source optical means 28 and a second optical path of said at least one scattered light collected by the detector optical means 29.

Figure 12D:
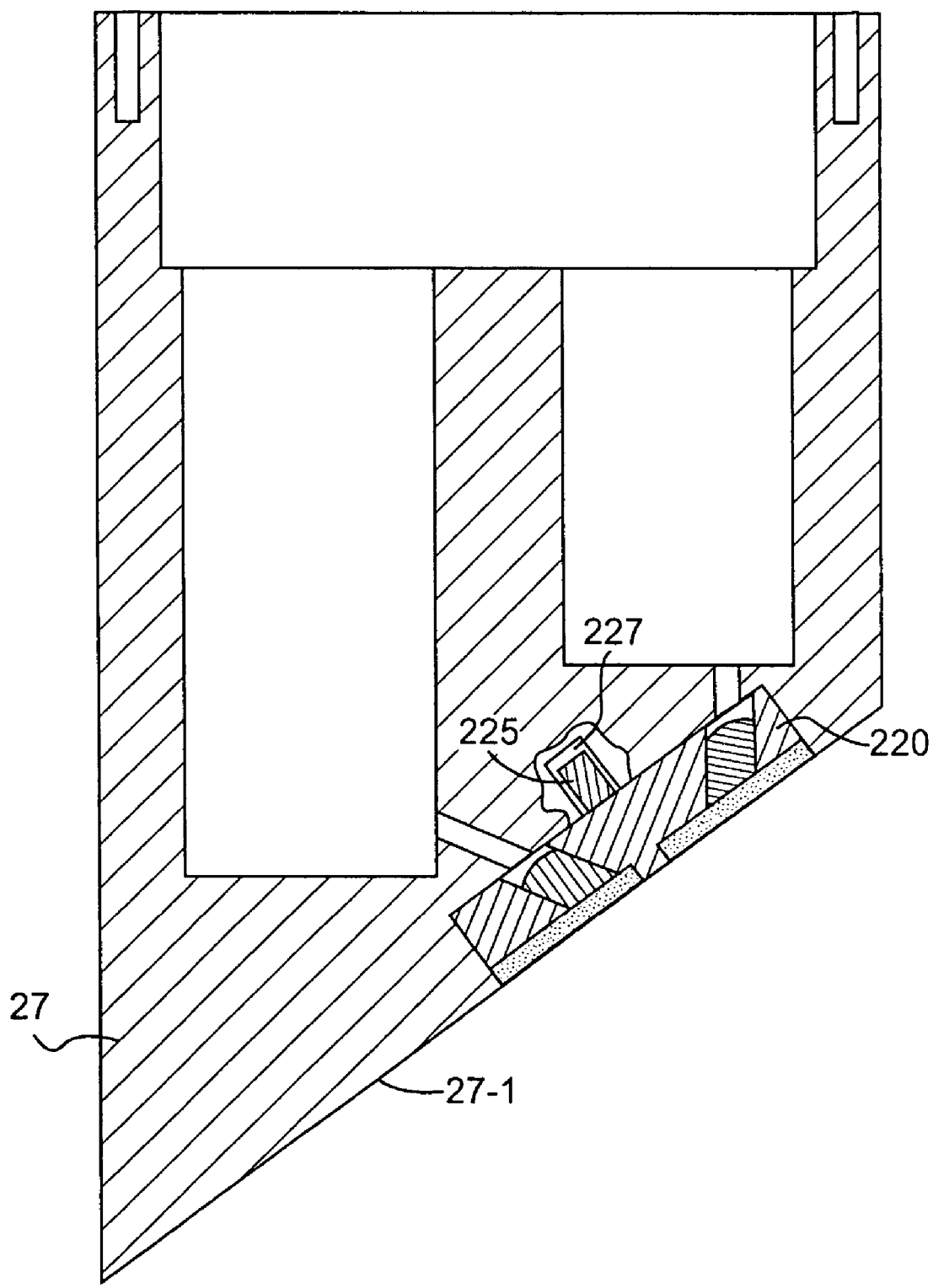
FIG. 12D shows the holder being positioned in the sensor according to the invention.

In another embodiment as shown in FIG. 12, the light focusing means 28-2 and the light focusing means 29-2 are included in an optical assembly 220 which has a pair of protective windows 221 placed inside a holder 222. The holder 222 is made of plastic and has on one side a small plastic barrier 223 to separate optically the light focusing means 28-2 and the light focusing means 29-2. Two tilted channels 224 are made to be connected with the channels 103, 105 respectively so as to accommodate the light focusing means 28-2 and the light focusing means 29-2 which are glued to the corresponding protective windows 221. On another side of the plastic holder 222 has positioning means, e.g., positioning screws, positioning pins 225 for positioning the optical means assembly 220 into the tilted bottom 27-1 of the sensor immersion body 27. The immersion body 27 has two positioning holes 227 for receiving the positioning pins 225. The optical means assembly 220 is glued to the immersion body 27 to provide a watertight assembly.

Figure 9:
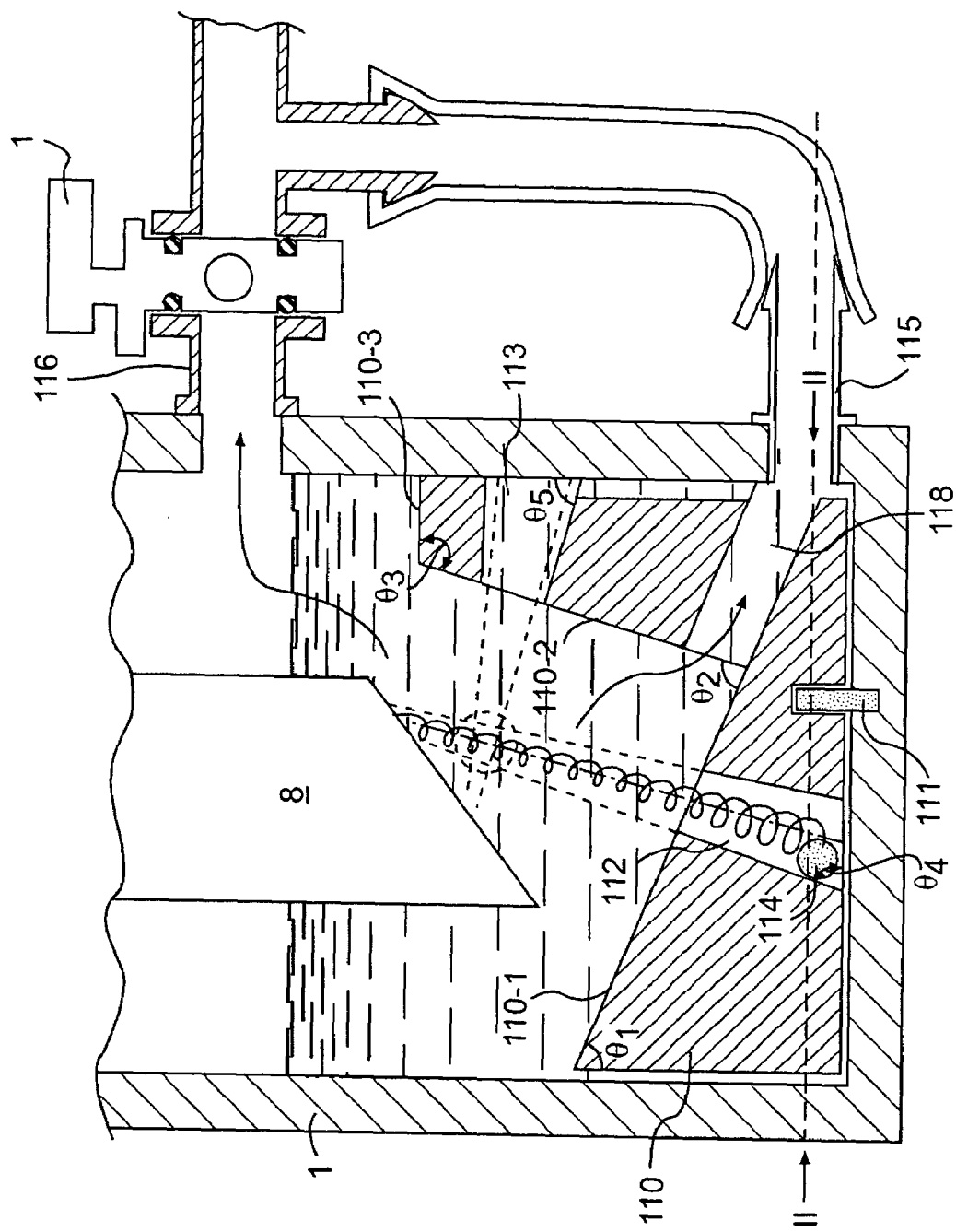
FIG. 9 shows a cross sectional view of a second embodiment of a turbidity sensor according to the invention.
Figure 10A:
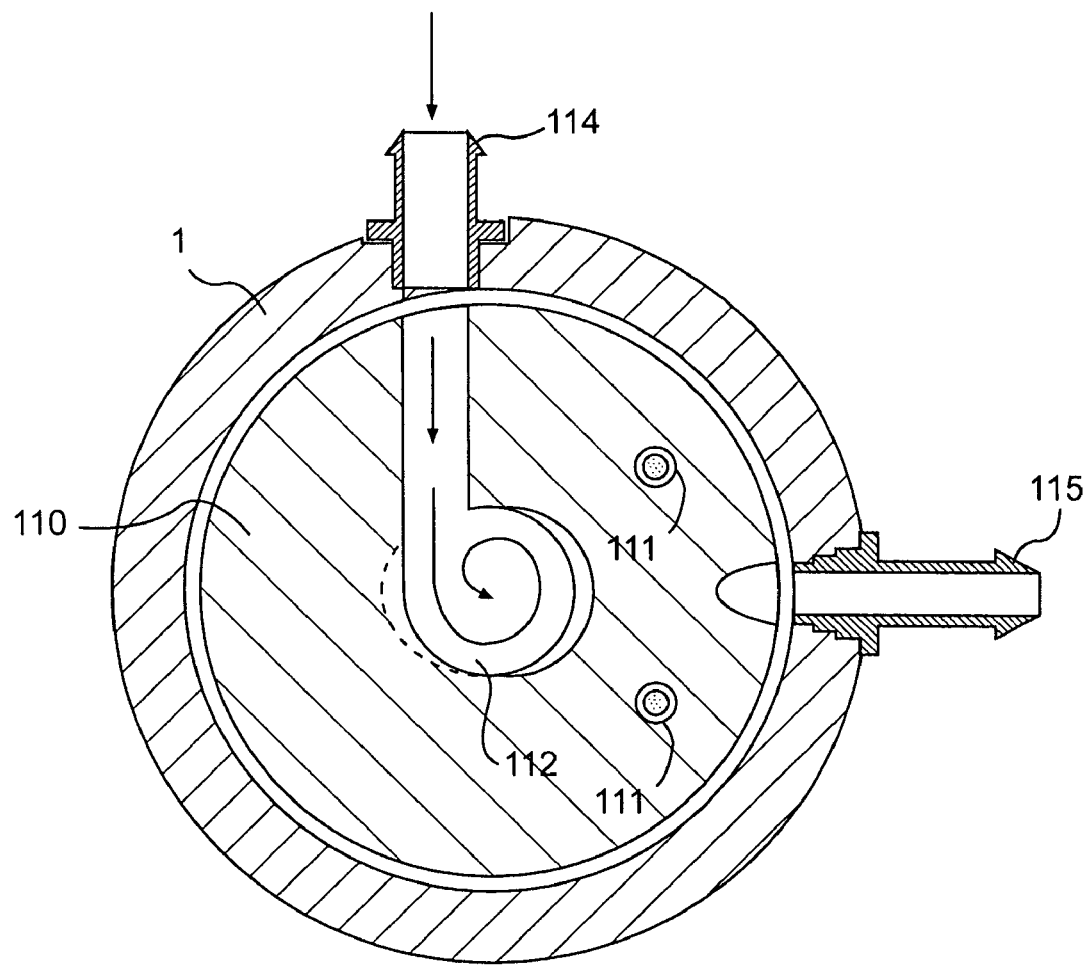
FIG. 10A shows a cross sectional view of a second embodiment of the turbidity sensor shown in FIG. 9 taken along the line II—II.
Figure 10B:
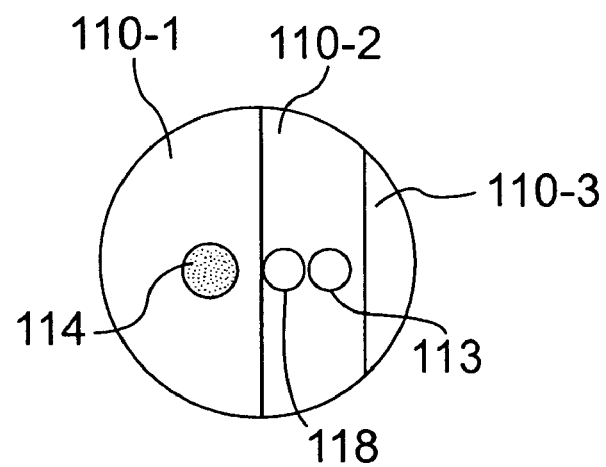
FIG. 10B shows a top view of an insert of the turbidity sensor shown in FIG. 9.

In another embodiment as shown in FIGS. 9–10, an insert 110 is placed at the bottom of the sample chamber 1 to increase testing efficiency. The insert 110 may be made by cutting a right angle valley away from the top of a solid column to form a slope 110-1 and a slop 110-2 while a flat peak 110-3 remaining intact as shown in FIG. 10B. An insert channel 112 extending form the bottom to the slope 110-1 is formed in the insert 110 and fluid-communicating with the inlet 121, and the insert channel 112 is angled toward the channel 104 to increase testing efficiency. An axle of the inlet 121 is set near the wall of an input channel in an insert 110 to form a vertex flow in the insert channel 112. An insert channel 113 extending form the wall of the sample chamber 1 to the slope 110-2 is formed in the insert 110 and angled toward the channel 105 to serve as a light trap so as to increase testing efficiency. The two insert channels 112, 113 have a reverse conical shape with cone angle approximately 12° and they are arranged along of the optical axes of the light source optical means 28 and the detector optical means 29 to serve as light traps for excitation beam from the light source optical means 28 and for eliminating reflections into the detector optical means 29. The addition of the insert 110 improves the sensitivity of the turbidity sensor form 0.1 NTU to 0.02 NTU. The channel 112 serves as a light trap as well as water inlet enables the sensor reacts 10 time faster than the turbidity sensors known in the art.

The insert 110 is made of an opaque material, such as aluminum or black PVC. The insert 110 has a diameter of 70 mm and a height of 60 mm. In FIG. 9, the slope 110-1 is 63 mm long, the slop 110-2 is 53 mm long, and the flat peak 110-3 is 4 mm long. The angles are respectively $\Theta 1=86°$, $\Theta 2=90°$, $\Theta 3=94°$, $\Theta 4=78°$, and $\Theta 5=78°$.

In this embodiment, two outlets 115, 116 are located at the different heights from the bottom of the sample chamber 1. The higher outlet 116 is equipped with a valve 117. The lower outlet 115 is connected with a third insert channel 118. The third insert channel 118 extends form the bottom of the chamber wall to the slope 110-2 is formed in the insert 110 and the insert channel 112 is angled in parallel with the slope 110-1 to increase testing efficiency. An inlet 114 guides the fluid sample 2 into the insert channel 112.

Figure 11B:
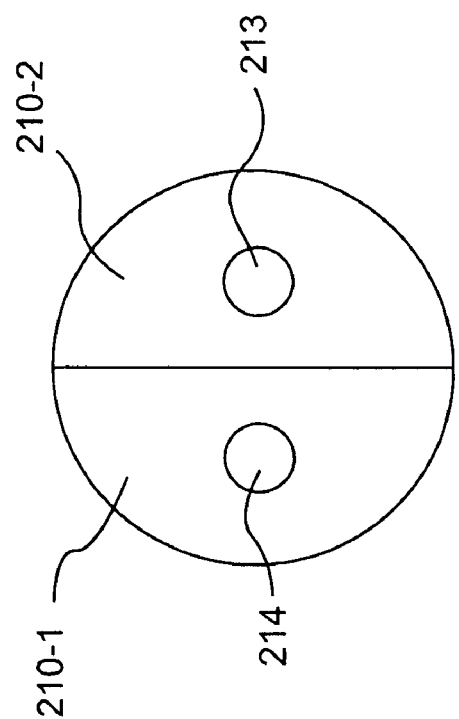
FIG. 11 shows a cross sectional view of a third embodiment of a turbidity sensor according to the invention.
Figure 11A:
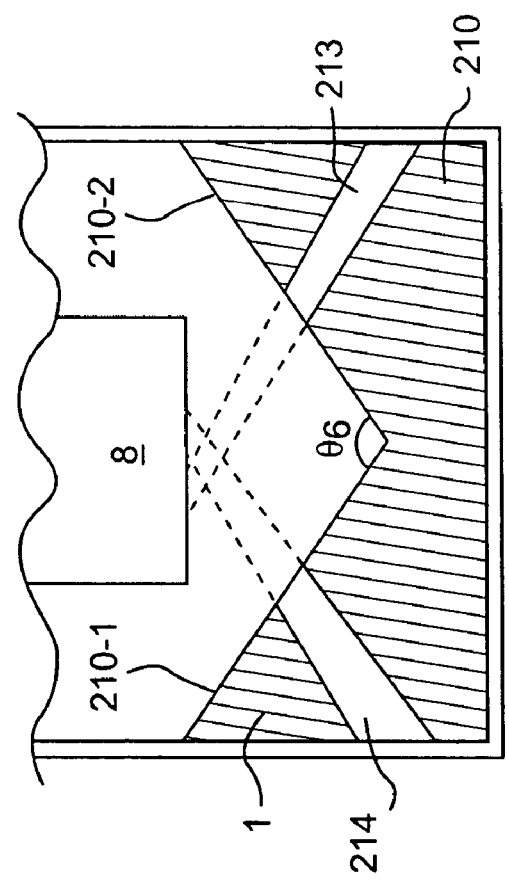

As shown in FIG. 11, an insert 210 may be made by cutting a right angle valley away at a center line of the top a solid column to form a slope 210-1 and a slop 210-2 as shown FIG. 11B to work with the turbidity sensor described in U.S. patent application Ser. No. 10/315,142. The slope 210-1 and the slop 210-2 form an angle $\Theta 6=90$ degrees. An insert channel 214 extending form the bottom to the slope 210-1 is formed in the insert 210 and fluid-communicating with a fluid inlet, and the insert channel 214 is angled toward the channel 104 to increase testing efficiency. An insert channel 213 extending form the wall of the sample chamber 1 to the slope 210-2 is formed in the insert 210 and angled toward the channel 105 to serve as a light trap so as to increase testing efficiency. The two insert channels 214, 213 have a reverse conical shape with cone angle approximately 12° and they are arranged along of the optical axes of the light source optical means 28 and the detector optical means 29 to serve as light traps for excitation beam from the light source optical means 28 and for eliminating reflections into the detector optical means 29. The tilted bottom part 27-1 of the invention outperforms the horizontal bottom part in U.S. patent application Ser. No. 10/315,142 by decreasing bubbles accumulated there under such that the tilted bottom part 27-1 does not have to be wiped as the horizontal bottom part to clean off the bubbles.

The principles, preferred embodiments and modes of operation of the present invention have been described in the foregoing specification. However, the invention, which is intended to be protected, is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents that fall within the spirit and scope of the present invention as defined in the claims, be embraced thereby.

What is claimed is:

1. A turbidity measuring system for measuring a sample liquid comprising:
   a chamber with at least one inlet and at least one outlet;
   a cover for covering the chamber;
   a sensor unit mounted on the cover, said sensor unit including:
   a watertight housing having a tilted bottom with respect to a sample liquid surface of the sample liquid, said watertight housing being placed below the liquid surface in the chamber when the sensor unit is in use;
   a light source;
   a first light focusing device for focusing a light emitted from the light source and passing therethrough into the liquid sample;
   a second light focusing device for collecting at least one scattered light resulted form the light passing into the liquid sample;
   a light detector for receiving the collected light thereby generating electronic signals; and
   a processor for converting the electronic signals into turbidity measuring units,
   wherein said watertight housing has two cavities for accommodating the light source and the light detector therein respectively, and two cylindrically-shaped channels for accommodating the first and second focusing devices therein respectively, the cylindrically-shaped channels are tilted away from the tilted bottom of said watertight housing at an angle symmetrically, and
   each of the cavities has a flat end tilting relatively to a cylinder axis thereof with the angle so as to be in parallel with the tilted bottom of said watertight housing.

2. The turbidity measuring system according to claim 1, wherein the inlet points toward an analytical area defined by overlapping a first optical path of the light emitted from the light source and then passing through the first light focusing device and a second optical path of said at least one scattered light collected by the second light focusing device.

3. The turbidity measuring system according to claim 1, wherein the cavities are cylindrically shaped and arranged in parallel.

4. The turbidity measuring system according to claim 1, wherein the tilted bottom is tilted with respect to the sample liquid at 45 degrees.

5. The turbidity measuring system according to claim 1, wherein the light source includes an incandescent lamp or an LED.

6. The turbidity measuring system according to claim 1, wherein the cylindrically shaped channels are tilted away from the tilted bottom of said watertight housing at 45 degrees.

7. The turbidity measuring system according to claim 1, wherein the chamber, the cover, and the watertight housing of the sensor are made of an opaque material to ensure that the light detector receives only the light from the second light focusing device.

8. The turbidity measuring system according to claim 1, wherein the opaque material is aluminum or black PVC.

9. A turbidity measuring system comprising:
   a chamber with at least one inlet and at least one outlet;
   a cover for covering the chamber;
   a sensor unit mounted on the cover, said sensor unit including:
   a watertight housing being placed below a liquid surface in the chamber when the sensor unit is in use;
   a light source;
   a first light focusing device for focusing a light emitted from the light source and passing therethrough into the liquid sample;
   a second light focusing device for collecting at least one scattered light resulted form the light passing into the liquid sample;
   a light detector for receiving the collected light thereby generating electronic signals, said light detector including at least two photodiodes for detecting separated turbidity measuring ranges; and
   a processor for converting the electronic signals into turbidity measuring units,
   wherein said watertight housing has cavities for accommodating the light source and the light detector therein respectively, and two cylindrically-shaped channels for accommodating the first and second focusing devices therein respectively, the channels are tilted away from a bottom of said watertight housing at an angle symmetrically, and
   each of the cavities has a flat end tilting relatively to a cylinder axis thereof with the angle so as to be in parallel with the bottom of said watertight housing.

10. The turbidity measuring system according to claim 9, wherein said separated turbidity measuring ranges include 0–20 NTU and 20–200 NTU.

11. The turbidity measuring system according to claim 9, wherein said at least two photodiodes include a first photodiode aligned with an axis of the channel accommodating the second light focusing device in order to measure more than 80% of scattered light collected by the second light focusing device, and a second photodiode placed right below the first photodiode to measure less than 10% of the scattered light collected by the second light focusing device.

12. The turbidity measuring system according to claim 9, further comprising a plate-shaped beam splitter, wherein said at least two photodiodes include first and second photodiodes having optical axes thereof cross each other at 90 degrees, and the beam splitter is placed between the first and second photodiodes with 45 degrees from the optical axes to provide a beam splitter-photodiode assembly.

13. The turbidity measuring system according to claim 12, wherein the beam splitter-photodiode assembly is placed after the second light focusing device such that the first photodiode collects more than 80% of scattered light collected by the second light focusing device and the second photodiode 90 collects less than 10% of the scattered light collected by the second light focusing device.

14. A turbidity measuring system comprising:
a chamber with at least one inlet and at least one outlet;
a cover for covering the chamber;
a sensor unit mounted on the cover, said sensor unit including:
a watertight housing being placed below a liquid surface in the chamber when the sensor unit is in use;
a light source;
a first light focusing device for focusing a light emitted from the light source and passing therethough into the liquid sample;
a second light focusing device for collecting at least one scattered light resulted form the light passing into the liquid sample;
a light detector for receiving the collected light thereby generating electronic signals; and
a processor for converting the electronic signals into turbidity measuring units,
wherein said watertight housing has two cavities for accommodating the light source and the light detector therein respectively, and two cylindrically-shaped channels for accommodating the first and second focusing devices therein respectively, the channels are tilted away from a bottom of said watertight housing at an angle symmetrically, and
each of of the cavities has a flat end tilting relatively to a cylinder axis thereof with the angle so as to be in parallel with the bottom of said watertight housing; and
an insert is placed at the bottom of the chamber having first and second insert channels each of whose axis pointing toward an axis of one of the cylindrically-shaped channels of the watertight housing in order to trap light.

15. The turbidity measuring system according to claim 14, wherein the first and second insert channels are cone-shaped.

16. The turbidity measuring system according to claim 14, wherein one of the first and second insert channels serves as the inlet of the chamber.

17. The turbidity measuring system according to claim 14, wherein the insert further includes a third insert channel fluid connecting with one of said at least one outlet of the chamber.

18. The turbidity measuring system according to claim 14, wherein the bottom of the watertight housing is tilted with respect to the sample liquid surface, and the insert is shaped by removing a right angle valley away from the top of a solid column to form a fist slope and a second slop, while leaving a flat peak at an edge of the column.

19. The turbidity measuring system according to claim 18, wherein $\Theta 1=86°$, $\Theta 2=90°$, $\Theta 3=94°$, $\Theta 4=78°$, and $\Theta 5=78°$.

20. The turbidity measuring system according to claim 14, wherein the bottom of the watertight housing is parallel with the sample liquid surface, and the insert is shaped by removing a right angle valley away from at a center line of the top of a solid column to form a fist slope and a second slop.

21. The turbidity measuring system according to claim 5, further comprising a reference detector for calibrating the light source.

22. The turbidity measuring system according to claim 21, further comprising a reference signal regulator for adjusting the reference detector to comply with a EPA or ISO normal value for a reference electrical signal of the reference signal regulator.

23. The turbidity measuring system according to claim 22, further comprising a controller which determines the incandescent lamp or the LED is in operation based by detecting the nominal value of the reference electrical signal of the reference signal regulator so as to automatically switch between a EPA or ISO processing.

24. A turbidity measuring system for measuring a sample liquid comprising:
a chamber with at least one inlet and at least one outlet;
a cover for covering the chamber;
a sensor unit mounted on the cover, said sensor unit including:
a watertight housing being placed below the liquid surface in the chamber when the sensor unit is in use, said watertight housing having two cavities for accommodating the light source and the light detector therein respectively;
a light source;
a focusing device holder having a first light focusing device for focusing a light emitted from the light source and passing therethrough into the liquid sample, a second light focusing device for collecting at least one scattered light resulted form the light passing into the liquid sample, two cylindrically-shaped channels for accommodating the first and second focusing devices therein respectively, and a positioning means for positioning the focusing device holder into a bottom of the watertight housing;
a light detector for receiving the collected light thereby generating electronic signals; and
a processor for converting the electronic signals into turbidity measuring units,
wherein the cylindrically-shaped channels are tilted away from the bottom of said watertight housing at an angle symmetrically, and
each of the cavities has a flat end tilting relatively to a cylinder axis thereof with the angle so as to be in parallel with the bottom of said watertight housing.

25. The turbidity measuring system according to claim 24, wherein the bottom of said watertight housing has at least one positioning hole for receiving the positioning means of the focusing device holder.

26. The turbidity measuring system according to claim 24, wherein the first light focusing device and the second light focusing device include prismatic lenses each having a spherical surface at one side and a flat tilted surface at another side.

27. The turbidity measuring system according to claim 24, wherein the focusing device holder has two windows optically communicating with the first light focusing device and the second light focusing device respectively, and said windows are separated by an opaque barrier.

28. The turbidity measuring system according to claim 27, wherein said opaque barrier and said windows are made as one unit glued to a bottom surface of said holder.

* * * * *